United States Patent
Martinent-Catalot et al.

(10) Patent No.: US 6,983,060 B1
(45) Date of Patent: Jan. 3, 2006

(54) METHOD TO MEASURE DEGREE AND HOMOGENEITY OF ALUMINA CALCINATION

(75) Inventors: Valerie Martinent-Catalot, Gardanne (FR); Jean-Michel Lamerant, Bouc-Bel-Air (FR); Bernard Rouit, Marseilles (FR)

(73) Assignee: Aluminium Pechiney, Paris Cedex (FR)

(*) Notice: Subject to any disclaimer, the term of this patent is extended or adjusted under 35 U.S.C. 154(b) by 681 days.

(21) Appl. No.: 10/130,260

(22) PCT Filed: Nov. 21, 2000

(86) PCT No.: PCT/FR00/03227

§ 371 (c)(1),
(2), (4) Date: Jul. 29, 2002

(87) PCT Pub. No.: WO01/38855

PCT Pub. Date: May 31, 2001

(30) Foreign Application Priority Data

Nov. 26, 1999 (FR) .................................. 99 14951

(51) Int. Cl.
*G06K 9/00* (2006.01)
*G01N 21/25* (2006.01)
*G01N 33/20* (2006.01)
*G01N 37/00* (2006.01)

(52) U.S. Cl. ........................ 382/100; 356/406; 73/61.42
(58) Field of Classification Search ................. 382/100
See application file for complete search history.

(56) References Cited

U.S. PATENT DOCUMENTS

| | | | |
|---|---|---|---|
| 3,844,780 A * | 10/1974 | Nelson et al. | 430/40 |
| 3,936,188 A * | 2/1976 | Sawyer | 356/36 |
| 3,941,874 A | 3/1976 | Payne | 423/489 |
| 5,303,310 A * | 4/1994 | Grove | 382/109 |

FOREIGN PATENT DOCUMENTS

EP 0 352911 1/1990

* cited by examiner

*Primary Examiner*—Joseph Mancuso
*Assistant Examiner*—Shefali Patel
(74) *Attorney, Agent, or Firm*—Dennison, Schultz, Dougherty & MacDonald

(57) ABSTRACT

A method for measuring degree and homogeneity of calcination of alumina utilizing an image analysis device equipped with a sensitive camera in a spectral analysis window corresponding to a wavelength range equal to or in the vicinity of visible light. The method includes the steps of mixing alumina under analysis in a liquid wherein the refractive index is, in the wavelength range, between the refractive index of a lightly calcined alumina and the refractive index of a strongly calcined alumina, preparing a slide for observation of the mixture in the image analysis device, the mixture being illuminated by stable polychromatic radiation compatible with the spectral analysis window, receiving an image by the camera and processing a signal resulting in the definition of an image composed of a given number of pixels with three calorimetric components, and statistically processing the pixels using their calorimetric components and determining the calcination degree and the homogeneity of the calcination.

6 Claims, 4 Drawing Sheets

METHOD TO MEASURE DEGREE AND HOMOGENEITY OF ALUMINA CALCINATION

FIELD OF THE INVENTION

The invention relates to an in-process monitoring method of the degree and homogeneity of alumina calcination.

The majority of technical aluminas involve, in their production process, a calcination step. Said step is determined to define the standard properties of the powder to be used in numerous applications (polishing, refractory concrete, fine ceramics, etc.). It is known that the calcination degree is well correlated with the surface area developed by the calcined alumina and, for the aluminas of interest to us, said surface area, measured using the BET method is typically between 0.5 and 5 $m^2/g$.

However, numerous applications and some target applications (ceramics, electronics, etc.) show the need for a more detailed analysis of these products, an analysis particularly giving information on the calcination homogeneity of the product; it is clear that two aluminas with a BET surface area equal to 1 $m^2/g$ for example but one of which is homogeneous and the other composed of a mixture of two aluminas at 0.5 and 1.5 $m^2/g$ will not have the same applicative properties.

STATE OF THE RELATED ART

During calcination, the alumina grains are converted into crystallite agglomerates of varying sizes depending on the degree of calcination.

To estimate the calcination degree achieved, it is possible to grind the alumina to the crystallite size and perform a granulometric analysis but this method is rarely or never used in practice since it is long and incompatible with the implementation of a method.

It is also possible to measure said calcination degree indirectly from the surface area developed by the alumina using a conventional method, such as the BET method. This method consists of measuring the quantity of nitrogen adsorbed over the entire surface area developed by the alumina. Said quantity increases with said surface area and the porosity of the grain (however, provided that the pores are open). It is used in production but it is long and does not give information on the heterogeneity of the calcination degree of the product.

Of the known analytical methods, image analysis may be used but it gives essentially dimensional information (grain size, shape factor) which is not correlated with the desired information (degree and homogeneity of calcination).

PROBLEM STATEMENT

The applicant tried to incorporate in the implementation of the alumina manufacturing method means to measure the degree and homogeneity of calcination.

Such means must be more rapid than the BET method in evaluating the average calcination degree and give information of the heterogeneity of the calcination degree of the alumina produced.

SUBJECT OF THE INVENTION

The invention firstly relates to a method to measure the degree and homogeneity of calcination of alumina comprising the use of an image analysis device equipped with a sensitive camera in a spectral analysis window corresponding to a wavelength range equal to or in the vicinity of visible light and comprising the following steps:

a) mixture of the alumina under analysis in a liquid wherein the refractive index is, in said wavelength range, between the refractive index of a lightly calcined alumina and the refractive index of a strongly calcined alumina;

b) preparation of a slide for observation of said mixture in said image analysis device, said mixture being illuminated by stable polychromatic radiation compatible with said spectral analysis window;

c) reception of the image by the camera and processing of the signal resulting in the definition of an image composed of a given number of pixels with three calorimetric components;

d) statistical processing of said pixels using their calorimetric components and used to give the calcination degree and the homogeneity of the calcination.

Indeed, the applicant started with the assumption that, by choosing to mix the alumina powder in a liquid with a mean refractive index between the extreme indices of a strongly calcined alumina and a lightly calcined alumina, it set up the best conditions to accentuate the differences in responses to a given lighting, typically visible light, and that theses differences in responses could be processed digitally and statistically to characterise the calcination degree of the alumina observed and the homogeneity of the calcination carried out on the alumina.

It obtained very encouraging results which are explained retrospectively as follows:

The refractive index of a substance varies as a function of the wavelength of the radiation passing through it. In the visible light range, this variation is much more significant for liquids than for solids. When a solid is immersed in a liquid with the same refractive index, no light dispersion or absorption takes place. However, if the refractive indices are different, a dispersion/absorption phenomenon is observed.

However, it is known that the refractive index of an alumina varies according to its degree of calcination. If an alumina immersed in a liquid is observed and if, for a given wavelength, the refractive index of the alumina and the liquid is not the same, a dispersion/absorption phenomenon takes place which is conveyed by a varying light intensity response.

When a solid, in this case alumina, is dispersed into a very large number of particles, the multiple facets are oriented in a random fashion with reference to the incident ray of light. Therefore, it is necessary to illuminate a large number of particles to obtain a significant statistical effect on the reflected (or transmitted) image.

If a polychromatic light—in the visible range for example—is used for illumination, the intensity response will differ according to the wavelength. The processing of the signal received by the camera makes it possible to obtain a coloured image that can be broken down into a multitude of pixels characterised by three colour components (according to the RGB system recommended in 1931 by Compagnie Internationale de l'Eclairage CIE, or according to the Lab system (or Hunt system), or according to any three-dimensional calorimetric space reference, etc.).

The applicant observed that the colour of each product, expressed in this way pixel by pixel in a three-dimensional calorimetric space, is characteristics of the product observed and that, by transferring the desired data to a histogram, it is possible to compare said histogram to "stand" histograms of known aluminas wherein the calcination degree can also be measured using the BET process.

In this approach, two steps make use of polychromatic radiation but the distinction that can be made between the spectral analysis window of the radiation illuminating the mixture and the visible spectrum used to describe the result of the processing of the signal received by the camera is clear.

The spectral analysis window may indeed correspond to the visible light spectrum but it may also correspond to a more restricted, continuous or discontinuous, wavelength range, or a range extended to the infra-red and ultra-violet ranges. The important factor is that the spectral analysis window is chosen such that the refractive indices of aluminas of varying degrees of calcination remain stable and that the refractive index of the liquid varies in this range, said range being sufficiently broad so that the refractive index of the liquid is between the refractive index lightly calcined alumina and the refractive index of a strongly calcined alumina. In addition, the order of magnitude of the wavelengths must in particular be less than that of the particle size, which makes it necessary to define a spectral analysis window in a wavelength range typically between 1000 Å and 10,000 Å, visible light (#4000–7000 Å) being for this reason well suited and enabling easy control of the measurement method. To facilitate the presentation, we will associate the spectral analysis window below with a visible light window and we will use the terms generally used for the observation of an object illuminated with visible light.

To prepare the observation, the alumina powder under analysis is mixed in a liquid of a given refractive index. As, in visible light, the refractive index of an under-calcined alumina is in the vicinity of 1.70 and the refractive index of an alumina α is in the vicinity of 1.76, a liquid with a refractive index in the vicinity of 1.73 is preferentially chosen. Such liquids, such as methylene iodide, are commercially available.

The mixture is deposited for example on a glass slide such as those used in optical microscopy. The slide is then placed in the observation field of the camera by means of a magnification system such that each particle can be represented by a sufficient number of pixels. Typically, with an image of 640*480 pixels, it is preferable to choose a magnification such that the image contains less than 1000 particles. However, said particles must be sufficient in number, since it is necessary to obtain a significant statistical effect on the image. The magnification system of an image analysis device used within the scope of the invention must make it possible to analyse an image comprising at least 50 particles.

The mixture is illuminated by a stable polychromatic radiation compatible with the spectral analysis window of the camera, i.e. the wavelength range of the reflected or transmitted radiation is included in the spectral analysis window of the camera.

The signal detected by the camera is processed such that an image defined by a given number of pixels with three calorimetric components is obtained. The image may contain a colour corresponding to the radiation detected by the camera but it may also have codified colours arbitrarily characterising the radiations detected—in this case, the term "false colours" is used. However, it is preferable to be able to use the entire range of the calorimetric space to define each pixel of the image.

The pixels, characterised by the three components or a calorimetric space, are then processed. Firstly, it is necessary to be certain that they correspond to particles since they are not contiguous in the mixture prepared on the slide and do not occupy the entire surface area of the image. Sorting may be carried out easily since the part of the image corresponding to background, i.e. occupied only by the liquid, shows a high light intensity. Therefore, it is possible to remove all the pixels wherein the three components are greater than a given value.

The remaining pixels are then represented in the calorimetric space. As the calcined alumina observed does not correspond to a perfectly homogeneous phase and as each pixel may in fact correspond to a plurality of photons of different energy, therefore to a mixture of colours, the representation in the calorimetric space of the pixels of the image correspond to a scatter of points varying in range. The applicant observed that, by choosing a liquid with a suitable diffractive index for the chosen spectral analysis window, it was possible to differentiate between aluminas using the scatters of points representing said aluminas in the calorimetric space, the location of said scatters being related to their calcination degree and the range of said scatters being related to their degree of homogeneity.

Using these representations in a three-component space, several types of statistical processing are possible. The purpose of the processing described here is to obtain a representation that is easier to interpret. It consists of situating the images under analysis with reference to the representative scatters of two known aluminas which are calcined at most different possible calcination degrees. For example, an α alumina and an under-calcined alumina, preferentially the least calcined but the most homogeneous possible, are chosen.

In principle, the two scatters corresponding to the alpha alumina and to the under-calcined alumina, respectively, are distinct from each other. Otherwise, it is preferable to choose another liquid and/or another spectral analysis window.

If the two scatters are distinct, it is possible to define a sub-space which "passes" through these scatters (an axis or a plane which passes through their centres of gravity, for example) and wherein the estimation of the calcination degree may be carried out using the "distances" between points, highlighted in said sub-space. In this way, it is possible to project the scatter of points of the alumina under analysis onto said sub-space and estimate the distance existing between said projection and that of the α alumina and/or that existing between said projection and that of the under-calcined alumina.

In this way, by illuminating the alumina+liquid mixture with visible white light, it is observed that a particle of α alumina gives a blue image and an under-calcined alumina gives a brown image of varying darkness. If the pixels were defined in the RGB reference system, it is attempted to classify them according to the "B-R" (blue less red) component. By classifying the number of pixels with a rising B-R component, a histogram or characteristic spectrum is obtained: the higher the calcination degree of the alumina, the more its spectrum is positioned to the right and, conversely, the lower the calcination degree of an alumina, the more its spectrum is located to the left.

The mean of the histogram obtained is characteristic of the calcination degree of the alumina analysed.

The standard deviation of the histogram obtained in this way is characteristic of the homogeneity of the calcination of the alumina analysed.

Secondly, the invention relates to the use of the measurement method described above to monitor the degree and homogeneity of calcination of alumina produced continuously in a ring furnace. Said measurement method is much more rapid that the BET method in determining the calcination degree of the alumina and makes it possible to react more rapidly to a deviation in the parameters of the furnace. This is particularly advantageous for a ring furnace working in continuous mode and producing several tonnes of alumina an hour. Finally, using this method, which is the only one known to date that makes it possible to determine the homogeneity of calcination, it is possible to correct the adverse effects of dust recycling which takes place in an untimely and poorly controlled fashion in ring furnaces and "contaminates" the alumina produced with an alumina of different grain size.

Using an alumina sample taken from the furnace, four slides are prepared. Each slide is observed at three different points using the claimed measurement method. Results that are reproducible to within 5% are obtained.

FIGURES

Figure 4:
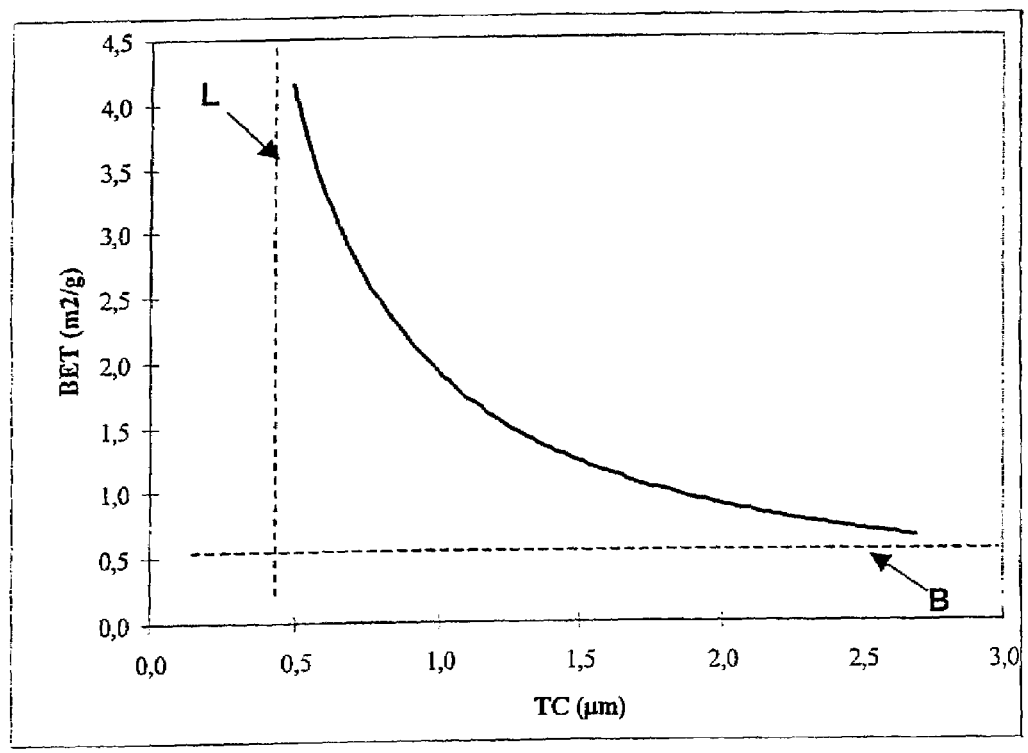

FIG. 4 gives the relationship between the BET surface area and the crystallite size TC expressed in $\mu m$.

Figure 5:
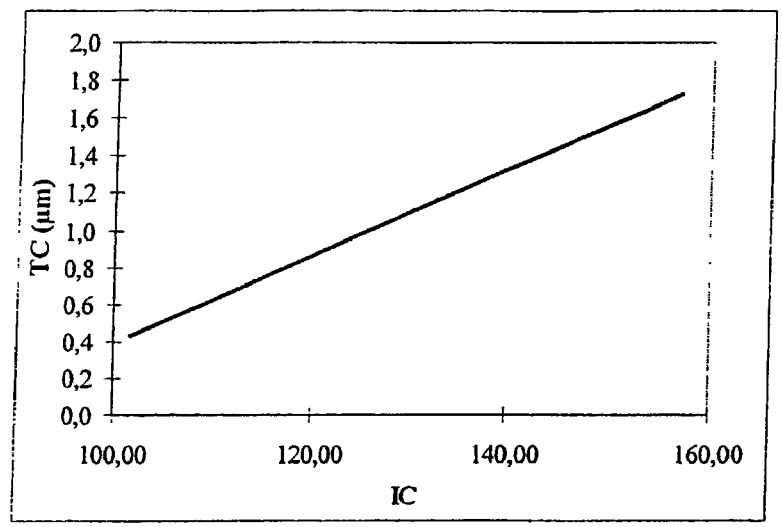

FIG. 5 shows this relationship in the range most specifically of interest to ceramists.

Figure 6:
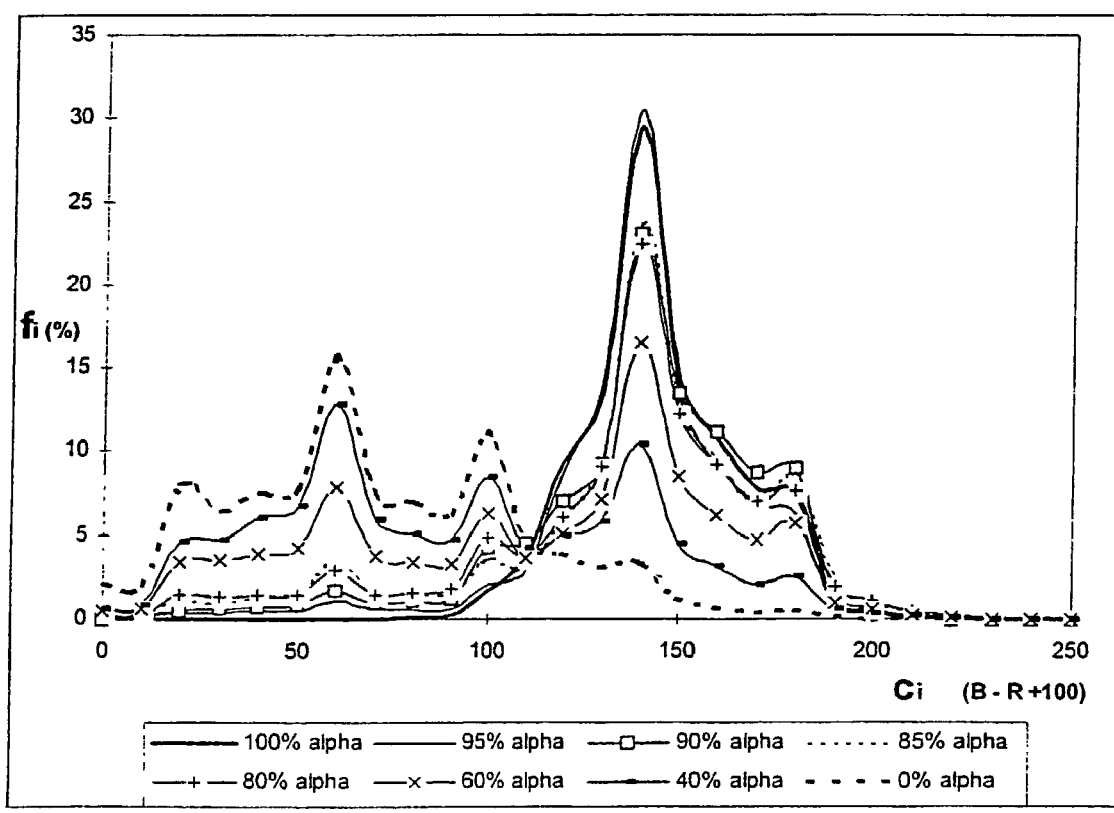

FIG. 6 shows the spectra obtained by mixing two aluminas of different degrees of calcination.

Figure 7:
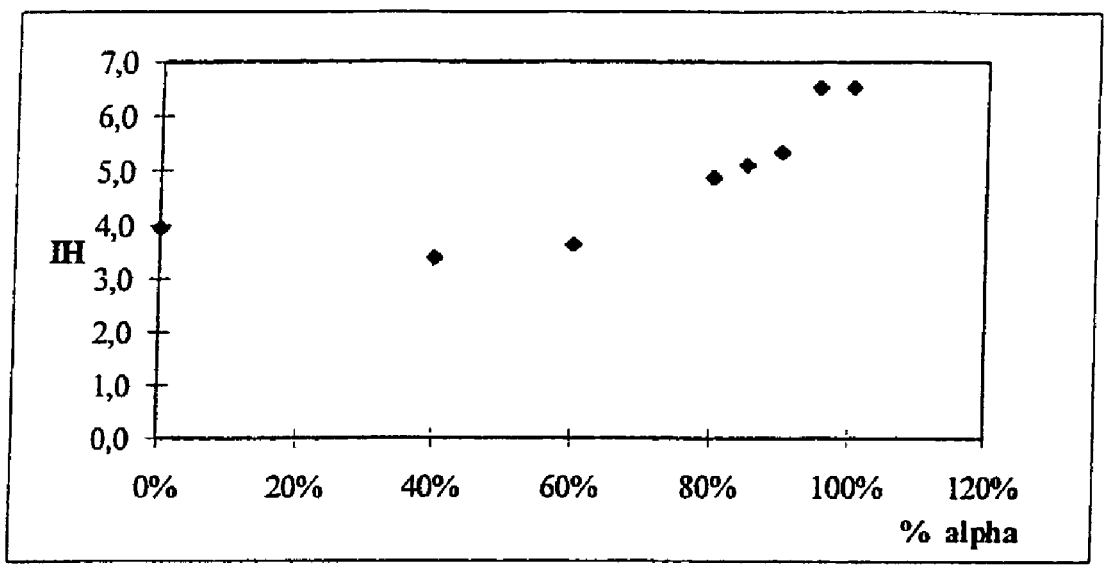

FIG. 7 shows, as a function of the percentage of one of the ingredients, the variation of the homogeneity index in a mixture of two aluminas, one strongly calcined and the other under-calcined.

EMBODIMENT OF THE INVENTION

Figure 1:
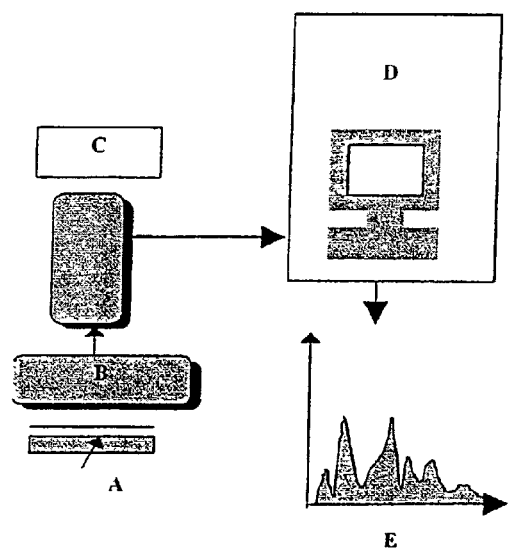
FIG. 1 illustrates the acquisition chain used within the scope of the example described below.

Acquisition Chain (FIG. 1)

The acquisition chain, represented in FIG. 1, is as follows:

1) The slide A on which the alumina/index liquid mixture is deposited must be prepared carefully: it is necessary to prevent the appearance of bubbles and obtain the most homogeneous particle distribution possible, said particles not being attached to each other. We selected a liquid with an index of 1.73. For industrial calcination monitoring in ring furnaces, this preparation may be automated.

2) Alumina grains being micronic, the use of a binocular microscope B with variable lenses according to the alumina is recommended. The aim is to obtain a sufficient quantity of grains for a valid statistical analysis (thus avoiding having to increase the number of tests).

3) The slides are illuminated with visible spectrum light. The setting and stability of the lighting are important since they affect the calorimetric components of the pixels of the image obtained by the camera C. It is particularly necessary to avoid saturate light intensity signals.

In this example, the camera is a mono-CCD matrix camera. A tri-CCD camera, which is more precise since it makes it possible to obtain the three basic colours (Red-Green-Blue) separately, is not necessary, but it makes it possible to access more detailed information resulting in a reduction in uncertainty on the measurements made with the colour images.

4) the data processing system D comprising a digitisation card used to digitise the information provided by the camera and offering numerous setting possibilities (colour, saturation, contrast, luminosity, etc.), the image processing application: it is used to perform acquisitions with the camera and then process the images in different formats (RGB, HSL, greyscale, etc.). A macro-instruction system enables the automatic acquisition processing operations. We used OPTIMAS.

the computer used is sufficiently powerful to process the images acquired (640*480 pixels*3 components). In this case, the computer used is a PC with 48 MB RAM.

5) The colour of each product is thus expressed pixel by pixel in a three-dimensional calorimetric space and each shade of colour may be transferred to a histogram using which the desired data may be extracted.

By classifying the pixels according to their components, a spectrum E is defined by projection on a particularly suitable axis to accentuate the differences in response. In this way, according to their degree of calcination, the grains appear throughout the axis. The mean of the spectrum can easily be linked with the mean degree of calcination, itself correlated with the BET surface area: in this way, each product range shows a specific spectrum appearance. In addition, the dispersion (spread of the curve) gives a reliable estimation of the heterogeneity of calcination of each product.

EXAMPLE OF APPLICATION

Chromatic Space Reference System: RGB, the Axis on Which the Spectrum is Projected being the B−R Axis In this reference system, the greater the blue component of the pixel, the more the corresponding part of the grain is considered to be calcined. Therefore, we calculated for each pixel the difference between the blue component (noted from 0 to 255) and the red component (as above) and recorded on the axis B−R+100 (difference between blue component and red component+100) the pixel populations corresponding to difference levels grouped in intervals of 10. The histograms obtained in this way have the same appearance as the characteristic spectra in FIG. 2, relating to three aluminas with different calcination degrees.

Alumina a is a metallurgic alumina, subject to light calcination, and a significant proportional of its grains have a blue component less than the red component: they are rather brown in appearance. On the other hand, alumina c is an alumina calcined in the presence of a mineralising agent. It comprises a majority of blue grains. Alumina b is an intermediate alumina which comprises a spectrum located between both extreme spectra. Alumina a, b and c comprise declining BET surface areas (a: 75 $m^2/g$; b: 3.9 $m^2/g$; c: 1.1 $m^2/g$). The products thus appear to be classified according to their calcination degree or, in reverse order, according to their BET surface area.

It is noted that some peaks are characteristics of the alumina family:

peak at 60: under-calcined grains, peak at 180: calcined grains.

Determination of Calcination Index

Figure 2:
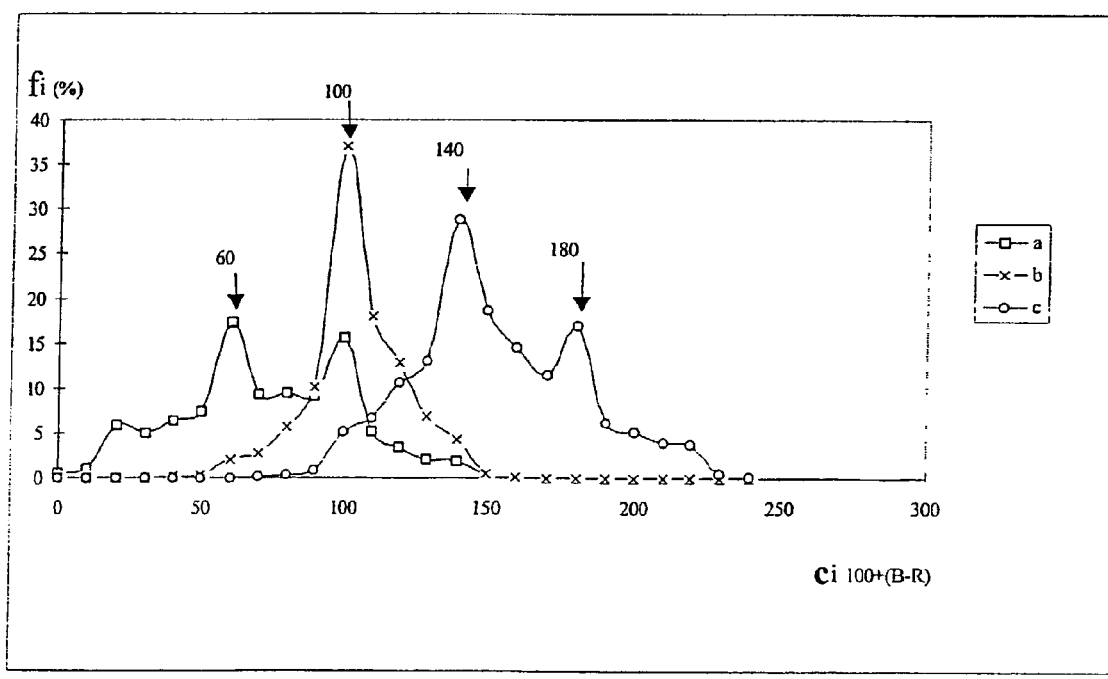
FIG. 2 represents three response spectra on the axis (B−R+100) relating to three aluminas (a, b, c) having different calcination degrees.

On the basis of spectra such as those in FIG. 2, it is possible to determine a calcination index IC;

If i is the classes from 0 to 260 (interval of 10), $f_i$ is the percentage and $c_i$ the value of the difference (blue component-red component+100) corresponding to each class i, the calcination index is defined by:

$$IC = \frac{\sum_{i=0}^{i=260} fi * ci}{100}$$

Figure 3:
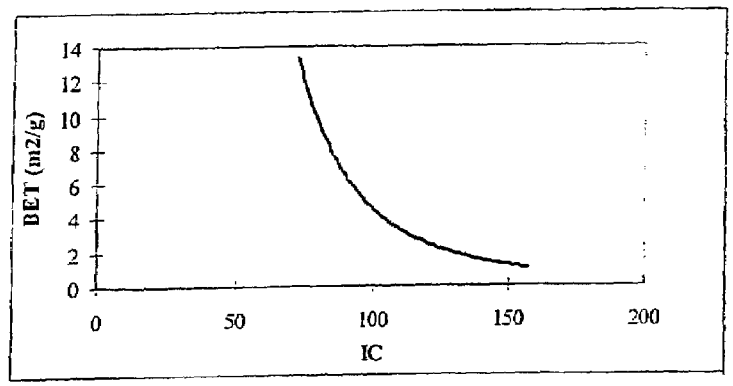
FIG. 3 shows the bijective relationship existing between the calcination index IC measured using the method according to the invention described in the example and the BET surface area expressed in $m^2/g$.

For all the products, a bijective correspondence between the calcination index IC and the BET values (FIG. 3) is found.

FIG. 4 shows a correlation conventionally defined between the BET surface area and the crystallite size TC—characterised here by the fine diameter d50 obtained by means of granulometry after grinding—in the range of interest to ceramists and refractory scientists (0.8 to 5 m2/g). This correlation is of the type:

$BET=A/(TC-L)+B$ where B (of the order of 0.5 m2/g) represents the analytical limit of the BET measurement and where L (of the order of 0.4 $\mu$m) represents analytical limit of the granulometric measurement.

Therefore, it is possible to correlate the calcination index IC with the crystallite size TC and, in the range of interest to ceramists and refractory scientists a linear equation: TC=A'·IC+B' (FIG. 5) is obtained. Such an equation is refined for each product range.

Determination of Homogeneity Index

The spectra of some products undergo more spreading than others and comprise varied grain colours. The homogeneity index was defined to account for the spreading and dispersion of such curves. The standard deviation of the frequencies was selected for one product family.

To illustrate the representative nature of this index, we prepared two products in the laboratory: one calcined (BET=1.4 m²/g) and one under-calcined (BET= 77 m²/g) that we mixed. The first (corresponding to "100% alpha" in FIG. 6) has a confined curve, the second (corresponding to "0% alpha" in FIG. 6) is more dispersed. The spectra obtained on different mixtures (corresponding to "x % alpha", where x is successively equal to 95, 90, 85, 80, 60 and 40) are presented in FIG. 6.

FIG. 7 shows, as a function of the percentage of calcined alumina (symbolised by "% alpha"), the variation in the homogeneity index IH of the different mixtures obtained. Note that any mixture comprising up to 70% calcined alumina has a lower homogeneity index than that of under-calcined alumina.

Advantages of the Method According to the Invention
  rapid and reliable response
  measurement method can be integrated into monitoring of calcined alumina production; in practical terms, the preparation of the sample requires some training but the determination of the coefficients IC and IH is automatic, enabling the operator to react rapidly in the event of a deviation in production parameters. This more rapid action has two beneficial effects: greater furnace flexibility and improved stability of calcination conditions. In this way, it is possible to gain 20% on out of specification products.

What is claimed is:

1. Method for measuring degree and homogeneity of calcination of alumina utilizing an image analysis device equipped with a sensitive camera in a spectral analysis window corresponding to a wavelength range equal to or in the vicinity of visible light and comprising the steps of:
  a) mixing alumina under analysis in a liquid wherein the refractive index is, in said wavelength range, between the refractive index of a lightly calcined alumina and the refractive index of a strongly calcined alumina;
  b) preparing a slide for observation of said mixture in said image analysis device, said mixture being illuminated by stable polychromatic radiation compatible with said spectral analysis window;
  c) receiving an image by the camera and processing a signal resulting in the definition of an image composed of a given number of pixels with three calorimetric components; and
  d) statistically processing said pixels using their calorimetric components and determining the calcination degree and the homogeneity of the calcination.

2. Method according to claim 1 wherein the spectral analysis window of the camera is the visible spectrum and wherein the refractive index of the liquid is chosen between 1.70 and 1.76.

3. Method according to claim 1 wherein the image analysis device comprises a magnification system such that it makes it possible to obtain images of said mixture containing between 50 and 1000 particles.

4. Method according to claim 1 wherein the images are defined by pixels with three RGB calorimetric components.

5. Method according to claim 4 wherein the pixels are classified according to a "B-R" (blue less red) component, a histogram obtained in this way having a mean and a standard deviation characteristic of the degree and homogeneity of calcination of the alumina observed in this way, respectively.

6. In a process for producing calcined alumina comprising sampling the calcined alumina to determine degree and homogeneity of calcination,
  the improvement comprising measuring the degree and homogeneity of the calcination utilizing an image analysis device equipped with a sensitive camera in a spectral analysis window corresponding to a wavelength range equal to or in the vicinity of visible light and comprising the steps of:
  a) mixing alumina under analysis in a liquid wherein the refractive index is, in said wavelength range, between the refractive index of a lightly calcined alumina and the refractive index of a strongly calcined alumina;
  b) preparing a slide for observation of said mixture in said image analysis device, said mixture being illuminated by stable polychromatic radiation compatible with said spectral analysis window;
  c) receiving an image by the camera and processing a signal resulting in the definition of an image composed of a given number of pixels with three calorimetric components; and
  d) statistically processing said pixels using their calorimetric components and determining the calcination degree and the homogeneity of the calcination.

* * * * *